United States Patent [19]

Hopkins

[11] Patent Number: 4,552,677
[45] Date of Patent: Nov. 12, 1985

[54] COPPER SALTS OF SUCCINIC ANHYDRIDE DERIVATIVES

[75] Inventor: Thomas R. Hopkins, Chesterland, Ohio

[73] Assignee: The Lubrizol Corporation, Wickliffe, Ohio

[21] Appl. No.: 571,247

[22] Filed: Jan. 16, 1984

[51] Int. Cl.$^4$ .............................................. C10M 1/54
[52] U.S. Cl. ..................................... 252/33.6; 252/35; 252/400.1
[58] Field of Search ....................... 252/33.6, 35, 400.1

[56] References Cited

U.S. PATENT DOCUMENTS

| | | | |
|---|---|---|---|
| 2,292,308 | 8/1942 | Watkins | 252/35 X |
| 2,320,392 | 6/1943 | White | 252/33.6 X |
| 2,363,514 | 11/1944 | Farrington et al. | 252/33.6 X |
| 2,458,425 | 1/1949 | Rocchini | 252/33.6 |
| 2,528,373 | 10/1950 | Knowles et al. | 252/35 X |
| 2,699,427 | 1/1955 | Smith et al. | 252/33.6 |
| 3,121,057 | 2/1964 | Gee et al. | 252/33.6 |
| 3,271,310 | 9/1966 | Lesuer | 252/35 |
| 3,649,661 | 3/1972 | Otto et al. | 252/33.6 X |
| 3,791,805 | 2/1974 | Brannen et al. | 252/35 X |
| 4,329,286 | 5/1982 | Heiba et al. | 252/33.6 X |

*Primary Examiner*—Jacqueline V. Howard
*Attorney, Agent, or Firm*—Walter C. Danison, Jr.; Denis A. Polyn

[57] ABSTRACT

Disclosed are compositions comprising a copper salt of a substituted succinic anhydride derivative containing at least one free carboxylic acid group, wherein said substituted succinic anhydride derivative contains a succinic anhydride derivative group and a substituent group wherein said substituent group is a hydrocarbon-based group containing from about 8 up to about 35 carbon atoms. Also disclosed are additive concentrates and lubricating compositions containing said compositions.

7 Claims, No Drawings

COPPER SALTS OF SUCCINIC ANHYDRIDE DERIVATIVES

FIELD OF THE INVENTION

This invention relates to compositions comprised of copper salts of substituted succinic anhydride derivatives. Typically, it relates to compositions comprised of copper salts of substituted succinic acid. It also relates to lubricating compositions and additive concentrates containing such compositions.

BACKGROUND OF THE INVENTION

In order to meet the demands required by today's lubricating oils, in particular, crankcase lubricating oils, there is a continuing effort to find new and improved lubricant additives. Such additives include antioxidants which permit the lubricating oil to withstand high temperatures without excessive breakdown of the oil and friction modifiers which reduce the friction between lubrication surfaces. Friction modifiers when used in the crankcase of an internal combustion engine reduce the engine's fuel consumption.

Copper oleate has been described in British Pat. No. 2,056,482 as an effective antioxidant. While copper oleate is an effective antioxidant in crankcase lubricants, the prior art failed to recognize that copper oleates cause degradation of the rust and copper/lead bearing corrosion performance of such lubricants. It has now been found that the copper salt compositions of the instant application are effective antioxidants for crankcase lubricants without the deleterious effect on rust and copper/lead bearing corrosion performance that accompanies copper oleate. Furthermore, the copper salt compositions of the instant application are effective friction modifiers.

DETAILED DESCRIPTION OF THE INVENTION

Basically, the invention is a composition comprising a copper salt of a substituted succinic anhydride derivative containing at least one free carboxylic acid group, wherein said substituted succinic anhydride derivative contains a succinic anhydride derivative group and a substituent group wherein said substituent group is a hydrocarbon-based group containing from about 8 up to about 35 carbon atoms.

THE SUBSTITUENT GROUP

The substituent group of the substituted succinic derivative compositions useful for the purposes of this invention are hydrocarbon-based groups.

As used herein, the term "hydrocarbon-based group" denotes a radical having a carbon atom directly attached to the remainder of the molecule and having predominantly hydrocarbon character within the context of this invention. Such groups include the following:

(1) Hydrocarbon groups; that is, aliphatic (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the molecule (that is, any two indicated substituents may together form an alicyclic radical). Such groups are known to those skilled in the art.

(2) Substituted hydrocarbon groups; that is, radicals containing nonhydrocarbon substituents which, in the context of this invention, do not alter the predominantly hydrocarbon character of the radical. Those skilled in the art will be aware of suitable substituents; examples are halo, alkoxy, hydroxy, alkylthio, carbalkoxy, nitro and carboxyl.

(3) Hetero groups; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbon-based group.

Terms such as "alkyl hydrocarbon-based group," "aliphatic hydrocarbon-based group," "aryl hydrocarbon-based group" and the like have meanings analogous to the above with respect to alkyl, aliphatic and aryl groups and the like.

Preferably, the hydrocarbon-based groups in the compositions of this invention are free from acetylenic unsaturation.

As used in the present specification and claims, the term "lower," when used in conjunction with terminology designating a chemical group such as alkyl, alkenyl, alkylene and the like, is intended to describe such groups having a total carbon atom content of up to and including 7. For example, "lower alkyl" includes all straight and branched chain alkyl groups of up to and including 7 carbon atoms.

Typically the substituent groups are aliphatic hydrocarbon-based groups containing from about 8 up to about 35 carbon atoms, preferably from about 10 up to about 30 carbon atoms and more preferably from about 12 up to about 28 carbon atoms. The substituent group may be a branch chain or straight chain configuration; however, it is preferred that at least 8 carbon atoms are in a straight chain configuration and, more preferably, is substantially straight chain configuration. Furthermore, the substituent group is preferably alkyl or alkenyl.

The term "substantially straight-chain" means that the group contains no more than about 2 methyl groups.

THE SUCCINIC ANHYDRIDE DERIVATIVE GROUP

As used herein, the term succinic anhydride derivative group is a radical which is a succinic acid group or functional derivative thereof. Typical of the succinic anhydride derivative groups are those selected from the group consisting of:

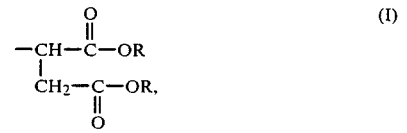

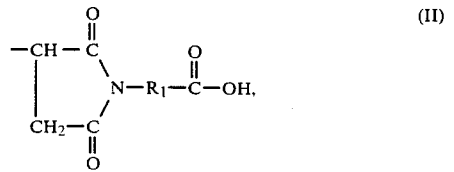

-continued

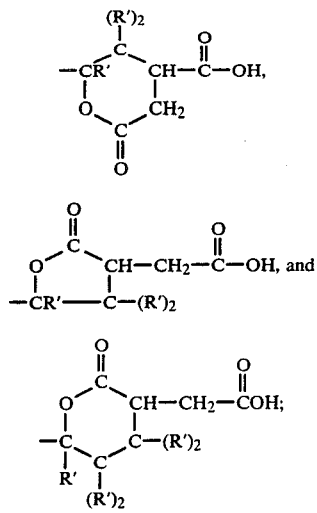

wherein each R is independently hydrogen or a hydrocarbon-based group containing up to about 18 carbon atoms, with the proviso that at least one R is hydrogen; $R_1$ is a lower alkyl radical; and each R' is independently hydrogen or a hydrocarbon-based group containing up to 27 carbon atoms, with the proviso that the total number of carbon atoms in the substituent group and the R' groups is no more than 35. Preferably R' is hydrogen.

A preferred succinic anhydride derivative group is the group having the following structure:

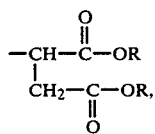

wherein each R is independently hydrogen or a hydrocarbon-based group containing up to about 18 carbon atoms with the proviso that at least one R is hydrogen; usually each R is independently hydrogen or an aliphatic hydrocarbon-based group containing up to about 10 carbon atoms, with the proviso that at least one R is hydrogen; preferably each R is independently hydrogen or a lower alkyl radical, with the proviso that at least one R is hydrogen.

A particularly preferred succinic anhydride derivative group is the succinic acid group of the formula:

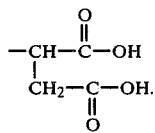

SUBSTITUTED SUCCINIC ANHYDRIDE DERIVATIVE

The substituted succinic anhydride derivative compositions useful for the purposes of this invention contain at least one free carboxylic acid group (i.e., —COOH). Free carboxylic acid groups may be in the substituent group or the succinic anhydride derivative group or in both. Usually, at least one free carboxylic acid group is present in the succinic anhydride derivative group. Preferably, these carboxylic acid groups are present only in the succinic anhydride derivative group.

Typically, the substituted succinic anhydride derivative useful for the purposes of this invention is derived from a substituted succinic anhydride. The substituted succinic anhydrides useful for the purposes of this invention are well known to those of ordinary skill in the art. Some of these substituted succinic anhydrides are described in U.S. Pat. Nos. 4,324,872; 4,158,664; 4,000,163; 3,819,660; 3,412,111; 3,382,172; and 2,411,215. These patents are hereby incorporated by reference for their teachings of substituted succinic anhydrides and methods for preparing such anhydrides.

The preferred substituted succinic anhydride derivative is the substituted succinic acid which is usually prepared by hydrolyzing the substituted succinic anhydride to the substituted succinic acid.

Another preferred substituted succinic anhydride derivative is the substituted succinic half-acid-half-ester having the derivative group of formula (I), wherein one R is hydrogen and the other R is a lower alkyl radical. These half-acid-half-esters are prepared by procedures known to those of skill in the art. Usually these are prepared by reacting one mole of substituted succinic acid with one equivalent (based on hydroxy groups) of alcohol in the presence of a catalyst with the removal of the water of reaction.

The substituted succinic anhydride derivative having the succinic anhydride derivative group of formula (II) is conveniently prepared by reacting a substituted succinic acid with a compound of the formula $H_2N$—$R_1$—COOH, wherein $R_1$ is defined hereinabove, under conditions suitable to remove the water of reaction resulting in the formation of the imide.

The substituted succinic anhydride derivative having the succinic anhydride derivative group of formula (III), (IV) or (V) represents the lactone derived from a substituted succinic acid of the formula:

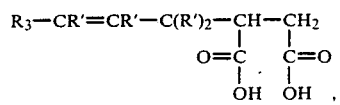

wherein $R_3$ is a hydrocarbon-based group and R' is as defined hereinabove.

Such lactones are formed by the acid catalyzed cyclization of one of the carbonyl groups into the β-8 unsaturation in the substituent group.

The methods for preparing the above-described substituted succinic derivative compositions are well known to those of ordinary skill in the art and further discussion herein is therefore unnecessary.

COPPER SALTS

The copper ions of the copper salts of this invention can be any of its possible oxidation states, although the most stable oxidation states are preferred, i.e., Cu(I) and Cu(II). The oxidation states are identified by their valence numbers. The oxidation state of +1 is identified by a valence of 1 (e.g., Cu having an oxidation state of +1 has a valence of 1 and is noted by the chemical symbol for copper followed by the (I), Cu(I)).

Copper has the oxidation states +1, +2 and +3; however, the oxidation state of +2 is the most stable and therefore the preferred oxidation state.

The copper salts of this invention can be prepared by procedures known to those of skill in the art. Therefore detailed discussion is unnecessary.

Generally, the copper salts of this invention can be prepared by reacting a substituted succinic anhydride derivative containing at least one free carboxylic acid group with a copper compound such as cupric acetate hydrate (Cu(C₂H₃O₂)₂·H₂O), basic cupric acetate (CuC₂H₃O₂)₂·CuO·6H₂O), cuprous carbonate, (Cu₂CO₃), basic cupric carbonate (CuCO₃Cu(OH)₂), cuprous hydroxide (CuOH) and cupric hydroxide (Cu(OH)₂). The substituted succinic anhydride derivative suitable for the purposes of this invention can be prepared separately and then reacted with the copper compound to prepare the copper salts of this invention. Alternatively, the derivative compositions can be prepared in situ. For example, a substituted succinic anhydride may be combined with water and the copper compound wherein the substituted succinic acid is prepared in situ which then reacts with the copper compound to form the salts of this invention.

The copper containing salts useful in this invention are acidic, neutral or basic salts. The acidic salts are those where there is less than one equivalent of copper for each equivalent of acid. The neutral salts are those where there is about one equivalent of copper for each equivalent of acid. The basic salts are those salts where there is more than one equivalent copper for each equivalent of acid.

For the purposes of this invention, one equivalent of copper is equal to the molecular weight of copper, 63.5, divided by the valence of the copper ion. For example, Cu(II) has an equivalent weight of 31.75 (63.5 divided by 2). Also, for the purposes of this invention, an equivalent of acid is equal to equivalent weight of the substituted succinic anhydride derivative which is determined by dividing the molecular weight of the derivative composition by the number of free carboxylic acid groups present in a derivative composition. For the purposes of this invention, the equivalent weight of the substituted succinic anhydride derivative is most conveniently determined by the formula:

$$\text{Equivalent weight} = \frac{56,100 \text{ (milligrams of KOH/equivalent)}}{\text{Acid Numbers of the substituted succinic anhydride derivative}}$$

The "acid number" of the substituted succinic anhydride derivative is defined, for purposes of this invention, as the number of milligrams of KOH used to raise the pH of one gram of sample under aqueous conditions to about 9.0. The pH can be determined by the use of an indicator that changes color in the range of 8.0–10.0 such as phenolphthalein or by electrical means such as a pH-meter.

Preferably the copper salts of this invention contain up to about one equivalent of copper for each equivalent of free carboxylic acid. More preferably, the copper salts contain from about 0.1 up to about 0.75 equivalent of copper per equivalent of free carboxylic acid. The most preferred copper salts are those containing about 0.5 equivalents of copper per equivalent of free carboxylic acid.

The preferred copper salt of this invention is a copper salt of a substituted succinic acid of the formula:

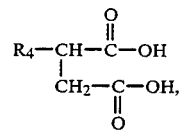

wherein $R_4$ is an aliphatic hydrocarbon-based group containing from about 8 up to about 35 carbon atoms. More preferably, these salts are Cu(II) salts and R is a substantially straight-chain alkenyl group containing from about 12 up to about 28 carbon atoms wherein there is about 0.5 equivalent of copper of each equivalent of carboxylic acid group in the succinic acid group.

The copper salts of this invention may be the salt of one substituted succinic anhydride derivative, but more commonly, they are mixtures of one or more substituted succinic anhydride derivatives.

This is particularly true since the substituent groups described herein are typically derived from commercially available materials (e.g., $C_{18-24}$ olefins) which are mixtures which when reacted with maleic anhydride result in mixtures of substituted succinic anhydrides having different carbon lengths in the substituent groups.

This invention is further exemplified in the following examples. Of course, these examples are not intended as limiting this invention as modification of the examples by ordinary expedient will be readily apparent to those of ordinary skill in the art.

In all the examples, unless otherwise stated, all parts are parts by weight and all percentages are derived from parts by weight.

EXAMPLE 1

Charged to a reaction vessel are 1372 parts (28 equivalents) of maleic anhydride and 5110 parts (14 equivalents) of a commercial mixture of $C_{18-24}$ olefins available from Ethyl Corporation wherein these olefins are typically 10 percent $C_{18}$, 45 percent $C_{20}$, 25 percent $C_{22}$ and 15 percent $C_{24}$ and are comprised predominately of substantially straight chain alpha, 1,1-disubstituted and 1,2-disubstituted olefins. The contents are heated to 175° C. and held at 175°–207° C. for 16 hours. The reaction mixture is distilled to 200° C. at 2–3 mm Hg. The reaction mixture is filtered to yield the desired substituted succinic anhydride having an acid number of 255.

EXAMPLE 2

Charged to a reactor are 198 parts (2.02 equivalents) of maleic anhydride and 500 parts (1.63 equivalents) of a commercial mixture of $C_{18-24}$ olefins described in Example 1. This reaction mixture is heated to 200° C. and held at 200°–220° C. for 10 hours. Unreacted starting materials are removed by vacuum distillation to 5 mm Hg at 200° C. The reaction mixture is filtered to yield the desired substituted succinic anhydride having an acid number of 290.

EXAMPLE 3

Charged to a reactor are 386 parts (2 equivalents) of the substituted succinic anhydride prepared in Example 2 and 60.1 parts (1 equivalent) of n-propyl alcohol. The reaction mixture is heated to 90° C. and held at 90°–102° C. for 2.5 hours. The reaction mixture is filtered to yield the desired ester product having an acid number of 126.

EXAMPLE 4

Charged to a reactor are 463 parts (4.72 equivalents) of maleic anhydride and 1000 parts (5.95 equivalents) of polypropylene tetramer. This reaction mixture is heated to 182° C. and held at this temperature for 9 hours. Unreacted starting materials are removed by vacuum distillation at 190° C. and 10 mm Hg. The reaction mixture is filtered to yield the desired substituted succinic anhydride having an acid number of 428.

EXAMPLE 5

Charged to a reactor are 501 parts of mineral oil, 9 parts water and 28.5 parts (0.26 equivalent) of basic copper (II) carbonate. This reaction mixture is heated to 65° C. and held at this temperature for 1 hour. Then, 193 parts (1 equivalent) of the substituted succinic anhydride prepared in Example 2 is added dropwise over 1.1 hours at 57°–91° C. The temperature is then increased to 140° C., and water is removed from the reaction by heating at this temperature for 0.75 hour. The reaction mixture is filtered to yield the desired product having a percent copper of 1.98.

EXAMPLE 6

Charged to a reactor are 220 parts (1 equivalent) of the substituted succinic anhydride prepared in Example 1, 18 parts water, 28.3 parts (0.26 equivalent) of basic copper (II) carbonate, 200 parts xylene, and 500 parts mineral oil. This reaction mixture is heated to 110° C. and 50 parts xylene is charged. The reaction is heated at reflux for 1 hour and a total of 15 parts water is removed through the use of a Dean Stark trap. The reaction material is distilled to 110° C. at 25 mm Hg. An additional 67 parts oil is charged and the contents are filtered to yield the desired product having a percent copper of 1.94.

EXAMPLE 7

Charged to a reactor are 193 parts (1 equivalent) of the substituted succinic anhydride prepared in Example 2, 347 parts mineral oil, 18 parts water, 49.9 parts (0.5 equivalent) copper (II) acetate monohydrate and 130 parts xylene. The reaction mixture is heated to reflux (155°–160° C.) while removing 38.5 parts water of reaction by azeotrope. The contents are filtered at room temperature and then vacuum distilled to 90° C. at 37 mm Hg. The material is again filtered to obtain the desired product having a percent copper of 2.28.

EXAMPLE 8

Charged to a reactor are 660 parts (3 equivalents) of the substituted succinic anhydride prepared in Example 1, 54 parts water, 150 parts (1.5 equivalents) copper (II) acetate monohydrate, 725 parts mineral oil, and 580 parts xylene. The reaction mixture is heated to reflux (145°–158° C.) while removing 111 parts water by azeotrope. The reaction mixture is stripped by vacuum distillation at 156° C. and 28 mm Hg. At 145° C. the contents are filtered to give the desired product having a percent copper of 3.4.

EXAMPLE 9

Charged to a reactor are 828 parts (4 equivalents) of the substituted succinic anhydride prepared in Example 2, 35 parts mineral oil, and 150 parts (2 equivalents) of glycine. This reaction mixture is heated to 160° C. with nitrogen blowing below the surface and 30 parts water is obtained. At 85° C., 110.5 parts (1 equivalent) of basic copper (II) carbonate is added to the reaction mixture over 30 minutes. The temperature is maintained at 95°–105° C. for four hours. The temperature is increased to 190° C. and volatiles are removed by blowing with nitrogen. The reaction mixture is filtered to yield the desired product having a percent copper of 4.61.

EXAMPLE 10

Charged to a reactor are 888 parts (2 equivalents) of the ester prepared in Example 3, 27.6 parts (0.25 equivalent) of basic copper (II) carbonate, 18 parts water, and 90 parts toluene. The reaction mixture is heated to 95° C. and refluxed for 19 hours. The reaction mixture is then vacuum distilled to 105° C. and 28 mm Hg. The reaction mixture is filtered to yield the desired product having a percent copper of 1.64.

EXAMPLE 11

Charged to a reactor are 888 parts (2 equivalents) of the ester prepared in Example 3. A 50% aqueous sodium hydroxide solution is charged over one hour. The addition is exothermic to 57° C. The reaction mixture is maintained at 57° C. for four hours. Thereafter, 200 parts of n-propyl alcohol and 249.7 parts (2 equivalents) of copper sulfate are added to the reaction mixture, and the temperature is increased to reflux and held for 40 hours. The reaction mixture is filtered and vacuum distilled to 130° C. and 20 mm Hg. The residue is the desired product having a percent copper of 5.04.

EXAMPLE 12

Charged to a reactor are 262 parts (2 equivalents) of the substituted succinic anhydride as prepared in Example 4, 345 parts of mineral oil, 199.7 parts (2 equivalents) copper (II) acetate monohydrate, 28.8 parts water and 172 parts xylene. The contents are heated to reflux (95°–98° C.) and held for 4.5 hours. Volatiles are removed by vacuum distillation to 182° C. at 17 mm Hg. At 135° C. the contents are filtered to obtain the desired product having a percent copper of 15.3.

EXAMPLE 13

Charged to a reactor are 880 parts (4 equivalents) of the substituted succinic anhydride prepared in Example 1. The reaction mixture is heated to 50° C. and 6.7 parts (0.12 equivalent) of concentrated sulfuric acid is charged over a 10 minute period. The temperature is increased to 90° C. and held for one hour. Then, 39.6 parts water is charged over 10 minutes at 90° C. and held at this temperature for 54 hours. At room temperature the contents are transferred to a separatory funnel and washed five times with 250 part portions of a 5% aqueous sodium chloride solution. Toluene (250 parts) is added and the remaining aqueous material is removed by azeotropic distillation. The organic volatiles are removed by vacuum distillation to 165° C. and 22 mm Hg. The reaction mixture is filtered at 100° C. to yield the desired substituted lactone acid.

EXAMPLE 14

A mixture of 302 parts (0.7 equivalent) of the substituted lactone acid prepared in Example 13, 70 parts (0.7 equivalent) of copper (II) acetate monohydrate, 200 parts xylene, and 324 parts mineral oil is heated to reflux (120° C.) and held for five hours. Volatiles are removed by vacuum distillation to 165° C. and 20 mm Hg. At 110° C. the material is filtered to yield the desired product having a percent copper of 3.43.

EXAMPLE 15

Charged to a reactor are 880 parts (4 equivalents) of the substituted succinic anhydride prepared in Example 1, 72 parts water, 245 parts (2 equivalents) copper (I) acetate, 300 parts mineral oil and 300 parts xylene. This reaction mixture is heated to a reflux of 145° C. while removing water azeotropically. Solvents are removed by vacuum distillation at 160° C. and 25 mm Hg. The reaction mixture is filtered at 150° C. to yield the desired copper (I) salt composition.

EXAMPLE 16

Charged to a reactor are 772 parts (4 equivalents) of the substituted succinic anhydride prepared in Example 2, 300 parts xylene, 250 parts mineral oil, 72 parts water and 245 parts (2 equivalents) of copper (I) acetate. The reaction mixture is heated to reflux (148°–157° C.) while removing water of reaction azeotropically. Volatiles are removed by vacuum distillation to 130° C. and 15 mm Hg. The reaction mixture is filtered to yield the desired copper (I) salt composition.

EXAMPLE 17

Charged to a reactor are 262 parts (2 equivalents) of the substituted succinic anhydride prepared in Example 4, 30 parts water, 122 parts (1 equivalent) of copper (I) acetate, 500 parts mineral oil, and 200 parts xylene. This reaction mixture is heated to reflux and held for three hours. Volatiles are removed by vacuum distillation to 175° C., at 17 mm Hg. The reaction mixture is filtered at 150° C. to yield the desired copper (I) salt composition.

As previously indicated, the copper salt of the compositions of this invention are useful as additives for lubricants in which they can function primarily as antioxidants and/or friction modifiers. They can be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Automatic transmission fluids, transaxle lubricants, gear lubricants, metal-working lubricants, hydraulic fluids and other lubricating oil and grease compositions can also benefit from the incorporation therein of the compositions of this invention.

Natural oils include animal oils and vegetable oils (e.g., castor, lard oil) liquid petroleum oils and hydrorefined, solvent-treated or acid-treated mineral lubricating oils of the paraffinic, naphthenic and mixed paraffinic-naphthenic types. Oils of lubricating viscosity derived from coal or shale are also useful base oils.

Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, poly(1-hexenes), poly(1-octenes), poly(1-decenes)); alkylbenzenes (e.g., dodecylbenzenes, tetradecylbenzenes, dinonylbenzenes, di(2-ethylhexyl)benzenes); polyphenyls (e.g., biphenyls, terphenyls, alkylated polyphenols); and alkylated diphenyl ethers and alkylated diphenyl sulfides and the derivatives, analogs and homologs thereof.

Alkylene oxide polymers and interpolymers and derivatives thereof where the terminal hydroxyl groups have been modified by esterification, etherification, etc., constitute another class of known synthetic lubricating oils. These are exemplified by polyoxyalkylene polymers prepared by polymerization of ethylene oxide or propylene oxide, the alkyl and aryl ethers of these polyoxyalkylene polymers (e.g., methyl-polyisopropylene glycol ether having an average molecular weight of 1000, diphenyl ether of poly-ethylene glycol having a molecular weight of 500–1000, diethyl ether of polypropylene glycol having a molecular weight of 1000–1500); and mono- and polycarboxylic esters thereof, for example, the acetic acid esters, mixed $C_3$–$C_8$ fatty acid esters and $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol and tripentaerythritol.

Silicon-based oils such as the polyalkyl-, polyaryl-, polyalkoxy-, or polyaryloxysiloxane oils and silicate oils comprise another useful class of synthetic lubricants; they include tetraethyl silicate, tetraisopropyl silicate, tetra-(2-ethylhexyl)silicate, tetra-(4-methyl-2-ethylhexyl)silicate, tetra-(p-tert-butylphenyl)silicate, hexa-(4-methyl-2-pentoxy)disiloxane, poly(methyl)siloxanes and poly(methylphenyl)siloxanes. Other synthetic lubricating oils include liquid esters of phosphorus-containing acids (e.g., tricresyl phosphate, trioctyl phosphate, diethyl ester of decylphosphonic acid) and polymeric tetrahydrofurans.

Unrefined, refined and rerefined oils can be used in the lubricants of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques, such as distillation, solvent extraction, acid or base extraction, filtration and percolation are known to those skilled in the art. Rerefined oils are obtained by processes similar to those used to obtain refined oils applied to refined oils which have been already used in service. Such rerefined oils are also known as reclaimed or reprocessed oils and often are additionally processed by techniques for removal of spent additives and oil breakdown products.

Generally the lubricants of the present invention contain a lubricating improving amount of one or more of the copper salt compositions of this invention, e.g., sufficient to provide it with improved oxidation stability or friction properties. In general, the lubricating compositions of this invention comprise a major amount of a lubricating oil and a minor amount of the copper salt compositions of this invention. Usually there will be an amount of copper salt sufficient to provide the lubricating oil with antioxidant properties. Normally the amount employed will be that amount of copper salt composition which will provide up to about 20 parts per million copper, preferably about 10 percent to about 180 percent parts per million copper, more preferably from about 20 up to about 120 parts per million copper and most preferably from about 50 up to about 100 parts per million copper of the total weight of the lubricating composition. Furthermore, typically the amount employed of the copper salts of this invention to achieve the desired levels of copper described above will be from about 0.01 percent up to about 0.5 percent, preferably from about 0.1 percent up to about 0.35 percent of the total weight of the lubricating composition. This amount is exclusive of solvent/diluent medium.

The invention also contemplates the use of other additives in combination with the copper salt compositions of this invention. Such additives include, for example, detergents and dispersants of the ash-producing or ashless type, supplemental corrosion- and oxidation-inhibiting agents, pour point depressing agents, extreme pressure agents, antiwear agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature about 50° C. and filtering the resulting mass. The use of a "promoter" in the neutralization step to aid the incorporation of a large excess of metal likewise is known. Examples of compound useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-β-naphthylamine, and dodecylamine.

A particularly effective method for preparing the basic salts comprises mixing an acid with an excess of a basic alkaline earth metal neutralizing agent and at least one alcohol promoter, and carbonating the mixture at an elevated temperature such as 60°–200° C.

Ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricant compositions of this invention. The following are illustrative:

(1) Reaction products of carboxylic acids (or derivatives thereof) containing at least about 34 and preferably at least about 54 carbon atoms with nitrogen containing compounds such as amine, organic hydroxy compounds such as phenols and alcohols, and/or basic inorganic materials. Examples of these "carboxylic dispersants" are described in British Pat. No. 1,306,529 and in many U.S. patents including the following:

| | | |
|---|---|---|
| 3,163,603 | 3,351,552 | 3,541,012 |
| 3,184,474 | 3,381,022 | 3,543,678 |
| 3,215,707 | 3,399,141 | 3,542,680 |
| 3,219,666 | 3,415,750 | 3,567,637 |
| 3,271,310 | 3,433,744 | 3,574,101 |
| 3,272,746 | 3,444,170 | 3,576,743 |
| 3,281,357 | 3,448,048 | 3,630,904 |
| 3,306,908 | 3,448,049 | 3,632,510 |
| 3,311,558 | 3,451,933 | 3,632,511 |
| 3,316,177 | 3,454,607 | 3,697,428 |
| 3,340,281 | 3,467,668 | 3,725,441 |
| 3,341,542 | 3,501,405 | 4,234,435 |
| 3,346,493 | 3,522,179 | Re 26,433 |

(2) Reaction products of relatively high molecular weight aliphatic or alicyclic halides with amines, preferably polyalkylene polyamines. These may be characterized as "amine dispersants" and examples thereof are described for example, in the following U.S. patents:

| | |
|---|---|
| 3,275,554 | 3,454,555 |
| 3,438,757 | 3,565,804 |

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. patents are illustrative:

| | | |
|---|---|---|
| 2,459,112 | 3,442,808 | 3,591,598 |
| 2,962,442 | 3,448,047 | 3,600,372 |
| 2,984,550 | 3,454,497 | 3,634,515 |
| 3,036,003 | 3,459,661 | 3,649,229 |
| 3,166,516 | 3,461,172 | 3,697,574 |
| 3,236,770 | 3,493,520 | 3,725,277 |
| 3,355,270 | 3,539,633 | 3,725,480 |
| 3,368,972 | 3,558,743 | 3,726,882 |
| 3,413,347 | 3,586,629 | 3,980,569 |

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. patents:

| 3,036,003 | 3,282,955 | 3,493,520 | 3,639,242 |
| --- | --- | --- | --- |
| 3,087,936 | 3,312,619 | 3,502,677 | 3,649,229 |
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,422 |

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. patents:

| 3,329,658 | 3,666,730 |
| --- | --- |
| 3,449,250 | 3,687,849 |
| 3,519,565 | 3,702,300 |

The above-noted patents are incorporated by reference herein for their disclosures of ashless dispersants.

Extreme pressure agents and corrosion- and oxidation-inhibiting agents are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate, phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

Many of the above-mentioned extreme pressure agents and corrosion-oxidation inhibitors also serve as antiwear agents. Zinc dialkylphosphorodithioates are a well known example.

Pour point depressants are a particularly useful type of additive often included in the lubricating oils described herein. The use of such pour point depressants in oil-based compositions to improve low temperature properties of oil-based compositions is well known in the art. See, for example, page 8 of "Lubricant Additives" by C. V. Smalheer and R. Kennedy Smith (Lezius-Hiles Co. publishers, Cleveland, Ohio, 1967).

Examples of useful pour point depressant are polymethacrylates, polyacrylates; polyacrylamides; condensation products of haloparaffin waxes and aromatic compounds; vinyl carboxylate polymers; and terpolymers of dialkylfumarates, vinylesters of fatty acids and alkylvinylethers. Pour point depressants useful for the purposes of this invention, techniques for their preparation and their uses are described in U.S. Pat. Nos. 2,387,501; 2,015,748; 2,655,479; 1,815,022; 2,191,498; 2,666,746; 2,721,877; 2,721,878; and 3,250,715 which are hereby incorporated by reference for their relevant disclosures.

Anti-foam agents are used to reduce or prevent the formation of stable foam. Typical anti-foam agents include silicones or organic polymers. Additional anti-foam compositions are described in "Foam Control Agents", by Henry T. Kerner (Noyes Data Corporation, 1976), pages 125–162.

The copper salt compositions of this invention can be added directly to the lubricant. Preferably, however, they are diluted with a substantially inert, normally liquid organic diluent such as mineral oil, naphtha, benzene, toluene or xylene, to form an additive concentrate. These concentrates usually contain from about 1 percent to 90 percent by weight of the copper salt composition of this invention and may contain, in addition, one or more other additives known in the art or described hereinabove. The remainder of the concentrate is the substantially inert normally liquid diluent.

The lubricating compositions of this invention are further exemplified by a base oil (95 percent by volume 150 Neutral lubricating oil and 5 percent by volume 150 Bright stock lubricating oil) containing 0.20 percent by weight of the product of Example 8.

The results shown in Table I hereinbelow exemplify the improved rust and corrosion performance of the copper salt antioxidants of the instant invention over the Cu oleate antioxidants of the prior art.

TABLE I

|  | IID (Engine Rust) | IIID (% Viscosity Increase) | L-38 (mg-Bearing Weight Loss) |
| --- | --- | --- | --- |
| 1 Lubricant containing 0.20% by weight of the product of Example 8* | 8.71 (pass) | 265 (pass) | 17.3 (pass) |
| 2 Lubricant containing 0.18% by weight of an oil solution of copper oleate containing 4% copper* | 7.95 (fail) | 246 (pass) | 112.9 (fail) |

*These lubricants are composed of the same base oils containing the same conventional lubricant additives in the same amounts.

As can be seen from Table I, the lubricating oils containing the copper salt of this invention (Lubricant 1) and the lubricating oil containing copper oleate (Lubricant 2) pass the Oldsmobile Sequence IIID oxidation test. However, in both the Oldsmobile sequence IID rust test and the CRC-L-38 Cu/Pb bearing corrosion test, the lubricant containing the copper salt of the instant invention passed, while the lubricant containing the copper oleate failed both these tests.

What is claimed is:

1. A composition comprising a copper salt of a substituted succinic anhydride derivative containing at least one free carboxylic acid group; wherein said substituted succinic anhydride derivative contains a succinic anhydride derivative group selected from the group consisting of:

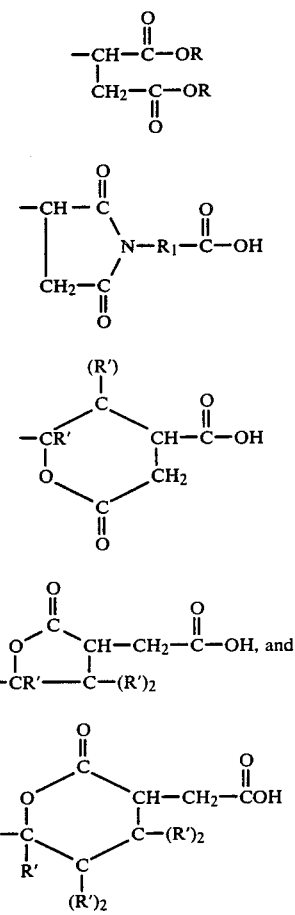

wherein each R is independently hydrogen or a hydrocarbon-based group containing up to about 18 carbon atoms, with the proviso that at least one R is hydrogen, $R_1$ is a lower alkyl radical, and, each R' is independently hydrogen or a hydrocarbon-based group containing up to 27 carbon atoms; and wherein said substituted succinic anhydride derivative contains a substituent group which is a hydrocarbon-based group with the proviso that the total number of carbon atoms in said substituent group and said R' groups is no more than 35.

2. A composition comprising a copper salt of a substituted succinic anhydride derivative wherein said substituted succinic anhydride derivative contains a substituent group and a succinic anhydride derivative group, wherein said substituent group is a substantially straight-chain alkenyl group containing from about 12 to about 28 carbon atoms, and wherein said succinic anhydride derivative group is selected from the group consisting of:

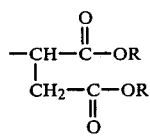

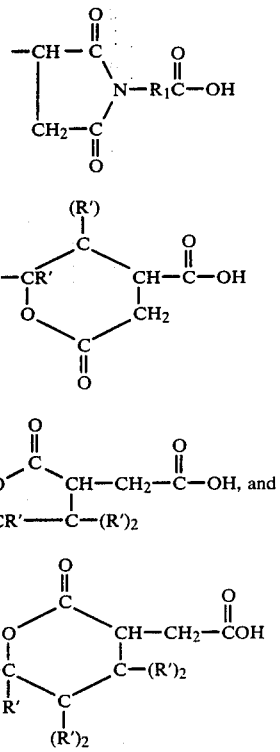

wherein each R is independently hydrogen or a hydrocarbon-based group containing up to about 18 carbon atoms, with the proviso that at least one R is hydrogen; $R_1$ is a lower alkyl radical; and, each R' is independently hydrogen or a hydrocarbon-based group containing up to 23 carbon atoms with the proviso that the total number of carbon atoms in the substituent group and the R' group is no more than 35, and wherein said copper salt contains from about 0.5 equivalent of copper for each equivalent of carboxylic acid group contained in said succinic anhydride derivative group.

3. A composition according to claim 2, wherein the substituent group is an aliphatic hydrocarbon group, free from acetylenic unsaturation, containing from about 10 up to about 30 carbon atoms, in which at least 8 carbon atoms are in a straight-chain configuration.

4. A composition according to claim 3, wherein R and R' are hydrogen and the substituent group is a substantially straight-chain alkyl or alkenyl group containing from about 12 up to about 28 carbon atoms.

5. A composition according to claim 4, wherein the copper salt contains up to about 1 equivalent of copper for each equivalent of free carboxylic acid group in the succinic anhydride derivative group.

6. An additive concentrate comprising a substantially inert, normally liquid organic diluent and from about 1 percent to about 90 percent by weight of a composition according to any of claims 1-5.

7. A lubricating composition comprising a major amount of a lubricating oil and a minor effective amount of a composition according to claims 1-5.

* * * * *